(12) United States Patent
Burton

(10) Patent No.: US 8,473,312 B2
(45) Date of Patent: Jun. 25, 2013

(54) DIAGNOSTIC IMAGE SECURITY SYSTEM

(75) Inventor: David Burton, Camberwell (AU)

(73) Assignee: Intellirad Solutions Pty Ltd., East Hawthorn, Victoria (AU)

( * ) Notice: Subject to any disclaimer, the term of this patent is extended or adjusted under 35 U.S.C. 154(b) by 149 days.

(21) Appl. No.: 12/465,742

(22) Filed: May 14, 2009

(65) Prior Publication Data

US 2009/0271216 A1    Oct. 29, 2009

Related U.S. Application Data

(63) Continuation of application No. 10/557,185, filed as application No. PCT/AU2004/000662 on May 19, 2004.

(30) Foreign Application Priority Data

May 19, 2003    (AU) ................................ 2003902422

(51) Int. Cl.
*G06Q 50/00*    (2012.01)
(52) U.S. Cl.
USPC .................................... 705/3; 705/2; 600/300
(58) Field of Classification Search
USPC ........................................................ 705/2, 3
See application file for complete search history.

(56) References Cited

U.S. PATENT DOCUMENTS

| | | | | |
|---|---|---|---|---|
| 5,740,428 A * | 4/1998 | Mortimore et al. | ................... | 1/1 |
| 5,876,926 A * | 3/1999 | Beecham | ........................... | 435/5 |
| 6,354,737 B1 * | 3/2002 | Hufe et al. | .................... | 378/205 |
| 6,556,698 B1 * | 4/2003 | Diano et al. | .................... | 382/132 |
| 6,574,742 B1 * | 6/2003 | Jamroga et al. | ............... | 713/400 |
| 6,988,075 B1 * | 1/2006 | Hacker | ............................. | 705/3 |
| 7,234,064 B2 * | 6/2007 | Menschik et al. | ............ | 713/193 |
| 2001/0048733 A1 * | 12/2001 | Schulze-Ganzlin | ............ | 378/62 |
| 2001/0051881 A1 * | 12/2001 | Filler | ................................ | 705/3 |
| 2002/0026331 A1 * | 2/2002 | Case | ................................. | 705/3 |
| 2004/0071038 A1 * | 4/2004 | Sterritt | ........................ | 365/232 |

FOREIGN PATENT DOCUMENTS

| | | |
|---|---|---|
| CA | 2333993 A1 | 12/1999 |
| WO | WO 99/13415 A1 | 3/1999 |
| WO | WO 01/95228 A1 | 12/2001 |

* cited by examiner

*Primary Examiner* — David Rines
(74) *Attorney, Agent, or Firm* — Morgan, Lewis & Bockius LLP

(57) ABSTRACT

A method for restricting unauthorised access to a patient's diagnostic images. Patient identification data is stored in a first database and diagnostic images associated with the patient are stored in a remote second database. The patient is issued with an access code which is provided to a user who is authorized by the patient to access the patient's diagnostic image. Use of the access code permits an authorized user to match the patient identification data retrieved from the first database with the associated diagnostic image stored in the second database.

24 Claims, 2 Drawing Sheets

DIAGNOSTIC IMAGE SECURITY SYSTEM

The present invention is a continuation application of application Ser. No. 10/557,185, with a §371 date of 16 Mar. 2006, which is a §371 National Stage Application of PCT Application No. PCT/AU2004/000662, filed 19 May 2004, which claims priority to Australian patent Application No. 2003902422, filed May 19, 2003, all of which are incorporated by reference.

FIELD OF INVENTION

The present invention broadly relates to methods and systems for restricting unauthorised access to patient medical records, and more particularly for restricting unauthorised access to diagnostic images.

BACKGROUND TO THE INVENTION

Diagnostic images generated by medical imaging technologies including radiography, magnetic resonance imaging (MRI) and computerized axial tomography (CAT), may be managed by computerised information systems such as Radiology Information Systems or Picture Archiving and Communications Systems (PACS). Such systems enable transmission of diagnostic images to remote physicians, clinics and hospitals.

For hospitals, enabling electronic distribution of diagnostic images overcomes the time, cost, and labour of producing and distributing film images and reports. However, security measures must be implemented to prevent unauthorised access to a patient's personal data.

The risk of patient images being accessed by unauthorised personnel is particularly relevant to the diagnostic imaging industry. Existing security measures include encryption devices, smart cards, electronic tags, mobile telephone interfaces, user identification and password prompts amongst a range of other security measures. Access to patient records and images needs to be restricted to consulting physicians and other authorised users who are directly involved in treating the patient.

Another security risk, which is unique to the diagnostic imaging industry is the problem of mismatching the diagnostic images of one patient with the patient identification and personal details of another.

Although images are scanned and prepared at a clinical or hospital diagnostic imaging facility, medical professionals at remote locations regularly require access to diagnostic images in order to discuss with patients the results or reports associated with their diagnostic images. Therefore, it is desirable to provide a secure means of transmitting or making available to consulting medical practitioners a patient's diagnostic images.

It is an object of the present invention to overcome or ameliorate one or more problems of the prior art.

SUMMARY OF THE INVENTION

According to a first aspect of the invention, there is provided a method for restricting unauthorised access to a patient's diagnostic images, the method including the following steps:
(a) storing patient identification data In a first database;
(b) storing a diagnostic image associated with the patient in a second database;
(c) issuing the patient with an access code; and
(d) providing the access code to a user authorised by the patient or a person designated by the patient to authorise access to the patients diagnostic image;
wherein use of the access code permits an authorised user to match the patient identification data retrieved from the first database with the associated diagnostic image stored in the second database.

The first database may be located on a portable storage medium. Preferably, the portable storage medium includes a smart card.

In one embodiment of the invention, the access code is stored on the portable storage medium together with the patient identification data.

Preferably, the second database is accessible to the authorised user over a network.

The access code may include a unique pixel sequence sample derived from the patient's diagnostic image. Preferably, a region in the patient's diagnostic image from which the unique pixel sequence sample is derived is indexed to ensure repeatability. The region in the patient's diagnostic image from which the unique pixel sequence sample is derived may be indexed in an access code header.

In a preferred form of the invention, extraction of the pixel sequence sample derived from the region of the patient's diagnostic image includes the step of scanning the region for a minimum level of pixel variation to ensure that the pixel sequence sample is unique to the patient's diagnostic image.

In an alternative embodiment of the invention, the diagnostic image is divided into more than one image segment, each image segment being stored separately and being associated with a unique access code, such that the entire diagnostic image is reconstructed only if a sequence of access codes is provided in a predetermined order.

According to a second aspect of the present invention, there is provided a system for restricting unauthorised access to a patient's diagnostic images, the system including:
(a) a first database for storing patient identification data;
(b) a second database for storing a diagnostic image associated with the patient;
(c) a processing component for generating an access code to be issued to the patient; and
(d) a transmission component for providing the access code to a user authorised by the patient or a person designated by the patient to authorise access to the patient's diagnostic image;
wherein the access code is required by the authorised user to match the patient identification data retrieved from the first database with the associated diagnostic image stored in the second database.

The first database may be located on a portable storage medium. Preferably, the portable storage medium includes a smart card.

In an embodiment of the invention, the access code is stored on the portable storage medium together with the patient identification data.

Preferably, the second database is accessible to the authorised user over a network.

The access code may include a unique pixel sequence sample derived from the patient's diagnostic image. Preferably, the system further includes a scanning component for scanning a region in the patients diagnostic image from which the unique pixel sequence sample is derived. More preferably, the scanning component scans the region for a minimum level of pixel variation to ensure that the pixel sequence sample is unique to the patient's diagnostic image.

BRIEF DESCRIPTION OF DRAWINGS

The invention will now be described in further detail by reference to the attached drawings illustrating example forms of the invention. It is to be understood that the particularity of the drawings does not supersede the generality of the preceding description of the invention. In the drawings.

DETAILED DESCRIPTION

Figure 1:
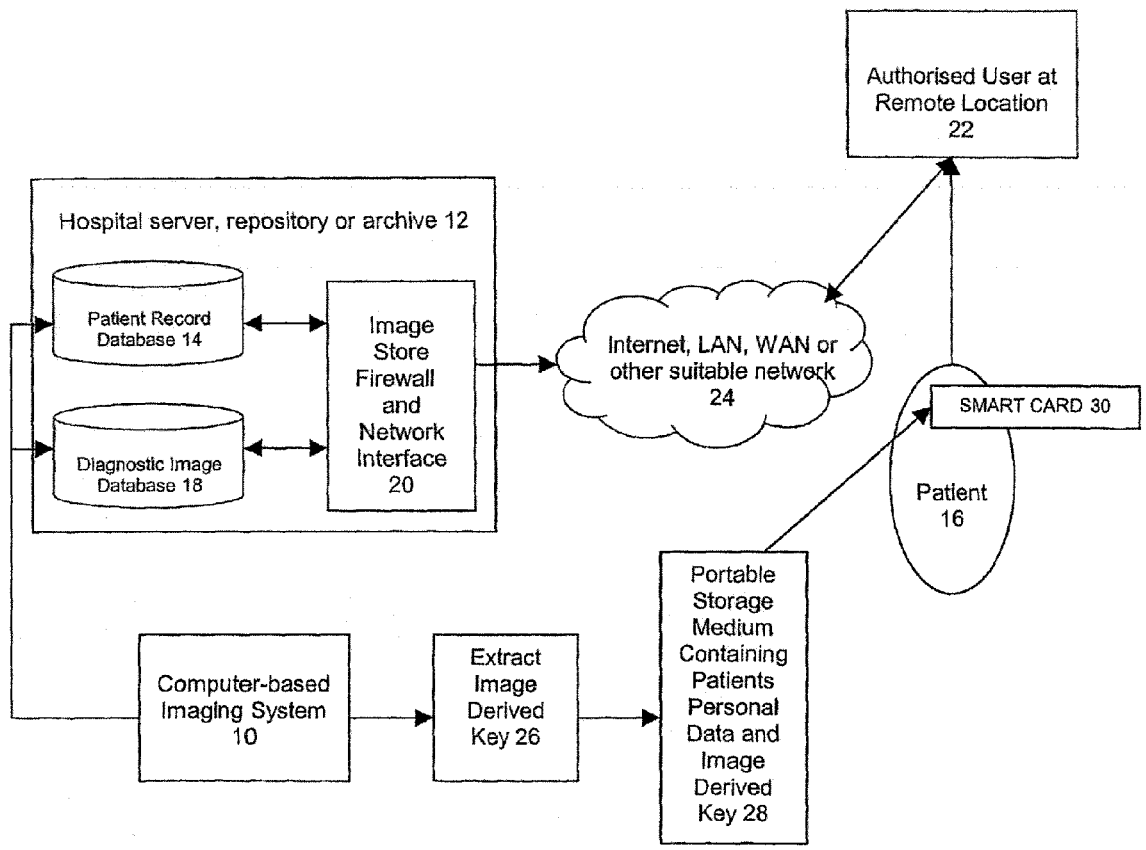
FIG. 1 is a schematic drawing indicating interaction between various components of the system in accordance with an embodiment of the present invention.

Referring firstly to FIG. 1, a radiology or other diagnostic imaging centre having a computer based imaging system 10, is located in a hospital or any other suitable healthcare service clinic 12. Patient data including personal identification and contact details are stored in a first patient record database 14. Any diagnostic image associated with the patient 16 including diagnostic images such as radiographs, magnetic resonance imaging (MRI), computerized axial tomography (CAT) scans and the like, are stored in a second database 18 which is independent from the first database containing patient data 14. The patient's personal data is stored separately from the patient's diagnostic image data files and the personal data and image data is not linked or associated in any way.

A consulting physician or other authorised user at a remote location 22, accesses the computer based imaging system 10 over the Internet, local area network (LAN), wide area network (WAN) or other suitable network 24.

The link between the first database storing the patient data 14 and the second database storing the diagnostic image files 18 is provided in the form of an access code which is generated and issued to the patient at the time that the diagnostic images are prepared. The patient 16 provides this access code to a user 22 who the patient authorises to access the patient's diagnostic images. Alternatively, the patient may authorise some other person, such as the patient's consulting specialist, to authorise access to the patient's diagnostic images. Therefore, the patient may provide his or her access code to the specialist who then provides the access code to other users who are authorised to access the patient's diagnostic images. Only use of the correct access code will permit the authorised user 22 to match the patient's identification data retrieved from the first database 14 with the associated diagnostic image stored in the second database 18. Therefore, unauthorised access of the patient's diagnostic images is prevented.

One suitable means of providing that the first database containing the patient's personal details 14 is isolated from the second database containing the patient's diagnostic image data 18, is to make one of the databases, for example, the diagnostic image database 18, accessible over a network such as the Internet 24, whilst the other, for example the patient database 14, is isolated from the network connection on a network isolated storage repository. Furthermore, the patient data could be additionally located on a portable storage medium 28 which can be carried by the patient 16. One suitable example of a portable storage medium includes a smart card 30.

The access code may be stored on the portable storage medium together with the patient identification data. This arrangement allows the patient 16 to simply provide his or her smart card 30 or other portable storage medium to the consulting physician or other authorised user 22. The authorised user 22 is thereby able to access the patient's personal data and to match the patient's personal data to the patient's diagnostic image using the access code. This ensures that the patient 16 has ultimate control over who is authorised to access the patient's personal data and diagnostic images.

The access code includes a unique pixel sequence derived from the patient's diagnostic image and is hereinafter referred to as an image derived key (IDK). Deriving the access code directly from the patient's diagnostic image 26 ensures integrity of a match between the patient personal data and the associated diagnostic image. Furthermore, the image derived key can be verified against the diagnostic image at any time in order to verify that the patient personal data has been matched to the correct diagnostic image.

The unique pixel sequence is derived from the patient's diagnostic image. Every diagnostic image will contain data which is unique to the patient from whom the diagnostic image was derived. Since no two patients are ever alike, it follows that no diagnostic image can be identical to any other diagnostic image. Even those diagnostic images which may appear the same to the unaided human eye will exhibit variations in the combination of data pixels present in a sample.

A reasonable pixel sample must be selected to give the desired result. A single pixel sample from a first diagnostic image could be identical to a single pixel sample from a second diagnostic image if the pixel samples are not selected in accordance with the following principles. Generally, in a series of diagnostic images analysed on a pixel per pixel basis, image composition will vary due to unique and unpredictable patterns or sequences of pixels. Selection of a "reasonable" sample requires that the sample should not be extracted from a region of the diagnostic image where the pixels are identical or exhibit only insignificant variation. Instances of insignificant or limited pixel variation can occur, for example, where the image is totally black, white or clear in the sample region, as may be observed in some non-physiological regions of a diagnostic image. Such non-physiological regions will occur, for example, in the outer border regions of a diagnostic image or within regions of images that have not been appropriately adjusted for optimal image quality (that is, the image exhibits problems with excessive or reduced contrast and/or brightness settings).

Figure 2:
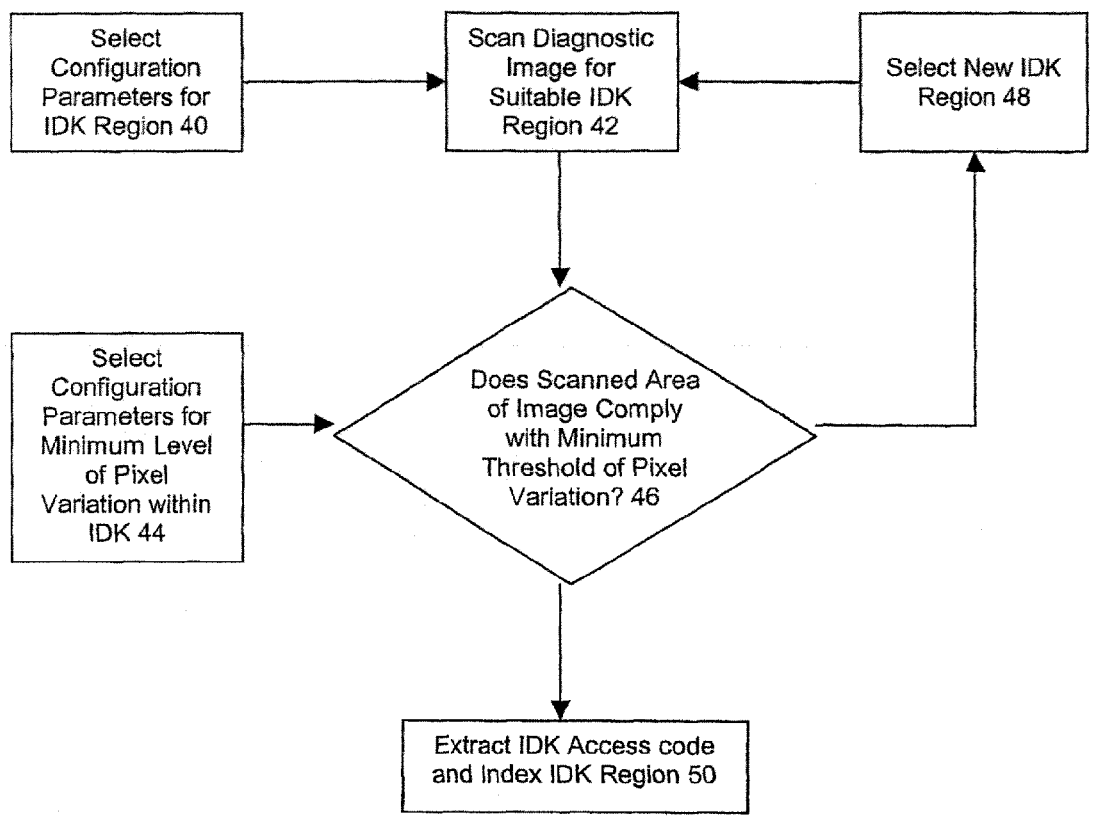
FIG. 2 is a flowchart outlining a process for deriving an image derived key for use according to an embodiment of the present invention.

Referring now to FIG. 2, the present invention provides a method for extracting an image derived key from a diagnostic image. Configuration parameters for selection of a suitable region of the image for extracting the image derived key (IDK) are determined 40. The diagnostic image is scanned to locate a suitable region for extracting the image derived key that complies with the configuration parameters 42. A check is made to establish that the selected region complies with a minimum level of pixel variation 46. The greater the level of pixel variation, the lower the probability that the image derived key could be used to decrypt a diagnostic image other than that from which the image derived key was extracted. The more complex the image derived key, the less likelihood exists that an unauthorised user could duplicate the image derived key. If the minimum threshold of pixel variation is not met, a new region of the image is selected and proposed for extraction of the image derived key 48. If the minimum level of pixel variation is met, then the image derived key is extracted from the image 50.

In addition, it is desirable to index the region of the diagnostic image from which the image derived key was extracted to ensure repeatability. This ensures that the region from which the image derived key was extracted, can be reliably located and rescanned for security validation at a later date. Indexing of the region of the diagnostic image from which the image derived key was extracted can be achieved by including an indicator of the region location within diagnostic image as part of an image derived key header.

In accordance with the method of the present invention, only the patient who has been diagnostically imaged or a user who has been assigned authorised access is provided with the image derived key containing the access code which provides the means to link the patient's diagnostic image with the patient's personal data.

The method described has particular application, for example, where a diagnostic image has been prepared on behalf of a patient, and the patient wishes to have the diagnostic image discretely provided to the patient's consulting practitioner for the purposes of discussing the patient's diagnosis. The patient is issued with an image derived key or access code at the time that the diagnostic image is prepared. The patient then provides the image derived key to the consulting practitioner to whom the patient wishes to grant access to his or her diagnostic image. This prevents the diagnostic image from having to be physically transported from one location to another, thereby reducing costs and negating the risk of the diagnostic image becoming damaged or lost during transit.

It is envisaged that an alternative embodiment of the present invention, could include division of each diagnostic image into more than one segment, each segment being stored independently of the other segment or segments, in different sections, servers, storage devices or the like. As the image is divided into the one or more segments, an image derived key is extracted from a region of each particular segment of the image. The entire diagnostic image is reconstructed only if a sequence of image derived keys is provided in a predetermined order.

This could involve a sequence of "rolling" or changing access codes being stored on a smart card, electronic tag or other coded access device. The coded access device contains the same sequence of access codes that were generated at the time that the original diagnostic image was segmented for storage. The coded access device therefore provides the patient with the sequence of code or rolling codes that need to be presented in a predetermined order for the patient's diagnostic image to be reconstructed.

It is an advantage of the present invention that no amount of network access or code breaking will be able to match the patient's personal data with the associated diagnostic image. Only use of the correct image derived key and authentication of the image derived key will allow the patient's identification data to be matched with the corresponding diagnostic image. Furthermore, the integrity of the patient data is maintained at all times, that is, it is not possible to match the patient's personal data to the incorrect diagnostic image since the image derived key which links the patient's personal data to the diagnostic image was extracted from and is verified against the diagnostic image.

It is to be understood that various additions, alterations and/or modifications may be made to the parts previously described without departing from the ambit of the invention.

The invention claimed is:

1. A method for restricting unauthorized access to a patient's diagnostic images, the method including the following steps:
    (a) storing patient identification data in a first database;
    (b) storing a diagnostic image associated with the patient in a second database;
    (c) generating an image derived key from a unique pixel sequence extracted from a first region of the patient's diagnostic image and associating the image derived key with the patient;
    (d) generating, by a processor, an access code header including the unique pixel sequence;
    (e) indexing each of the patient identification data stored in the first database and the diagnostic image associated with the patient in the second database with the access code header;
    (f) receiving the image derived key from an authorized user; and
    (g) securely retrieving, by a processor, the diagnostic image by matching, the image derived key to the access code header of the indexed patient identification data from the first database and to the access code header of the diagnostic image stored in the second database.

2. A method according to claim 1, wherein the first database is located on a portable storage medium.

3. A method according to claim 2, wherein the portable storage medium includes a smart card.

4. A method according to claim 2, wherein the image derived key is stored on the portable storage medium together with the patient identification data.

5. A method according to claim 1, wherein use of the image derived key enables an authorized user to match the patient identification data retrieved from the first database with the associated diagnostic image stored in the second database, and the second database is accessible to the authorized user over a network.

6. A method according to claim 1, wherein the first region in the patient's diagnostic image from which the unique pixel sequence is derived is indexed to ensure repeatability.

7. A method according to claim 6, wherein the indexing occurs in a header of the image derived key.

8. A method according to claim 1, wherein extraction of the unique pixel sequence derived from the first region of the patient's diagnostic image includes scanning the region for a minimum level of pixel variation to ensure that the pixel sequence is unique to the patient's diagnostic image.

9. A method according to claim 1, further comprising dividing the diagnostic image into more than one segment and generating an image derived key for each of the diagnostic image segments, wherein more than one image derived key is generated for the entire diagnostic image and the entire diagnostic image is reconstructed only if a sequence of the more than one image derived key is provided in a predetermined order.

10. A system for restricting unauthorized access to a patient's diagnostic images, the system including:
    (a) a first database for storing patient identification data;
    (b) a second database for storing a diagnostic image associated with the patient;
    (c) a processing component for
        generating an image derived key from a unique pixel sequence extracted from a first region of the patient's diagnostic image and associating the image derived key with the patient,
        generating an access code header including the unique pixel sequence
        indexing each of the patient identification data stored in the first database and the diagnostic image associated with the patient in the second database with the access code header,
        receiving the image derived key from an authorized user, and
        securely retrieving the diagnostic image by matching, the image derived key to the access code header of the indexed patient identification data from the first database and to the access code header of the diagnostic image stored in the second database; and
    (d) a transmission component for providing the image derived key to a user authorized by the patient to access the patient's diagnostic image; wherein the image derived key is required by the authorized user to match the patient identification data retrieved from the first database with the associated diagnostic image stored in the second database.

11. A system according to claim 10, wherein the first database is located on a portable storage medium.

12. A system according to claim 11, wherein the portable storage medium includes a smart card.

13. A system according to claim 11, wherein the image derived key is stored on the portable storage medium together with the patient identification data.

14. A system according to claim 10, wherein the second database is accessible to the authorized user over a network.

15. A system according to claim 10, further including a scanning component for scanning the first region in the patient's diagnostic image from which the unique pixel sequence is derived.

16. A system according to claim 15, wherein the scanning component scans the first region for a minimum level of pixel variation to ensure that the pixel sequence is unique to the patient's diagnostic image.

17. A method according to claim 1, further comprising the step of verifying the image derived key against the patient's diagnostic image.

18. A method according to claim 8, wherein the minimum level of pixel variation is associated with a low probability that the image derived key corresponds to another patient diagnostic image.

19. A method according to claim 8, wherein the scanning the first region for a minimum level of pixel variation is repeated in a second region of the patient's diagnostic image.

20. A method according to claim 8, wherein the scanning the region for a minimum level of pixel variation is repeated in a second region when the minimum level of pixel variation in the first region is not met.

21. A system according to claim 10, further comprising a verification component for verifying the image derived key against the patient's diagnostic image.

22. A system according to claim 16, wherein the minimum level of pixel variation is associated with a low probability that the image derived key corresponds to another patient diagnostic image.

23. A system according to claim 16, wherein the scan of the first region for a minimum level of pixel variation is repeated in a second region of the patient's diagnostic image.

24. A system according to claim 16, wherein the scan of the region for a minimum level of pixel variation is repeated in a second region when the minimum level of pixel variation in the first region is not met.

* * * * *